(12) United States Patent
Hawk et al.

(10) Patent No.: US 12,178,926 B2
(45) Date of Patent: Dec. 31, 2024

(54) FACILITY DESIGN TO MINIMIZE VIRAL LOAD

(71) Applicant: Ampersand Intelligence, Newport Beach, CA (US)

(72) Inventors: Kristina Elizabeth Hawk, Newport Beach, CA (US); Robert S. Bray, Jr., Newport Beach, CA (US)

(73) Assignee: Ampersand Intelligence, Newport Beach, CA (US)

(*) Notice: Subject to any disclaimer, the term of this patent is extended or adjusted under 35 U.S.C. 154(b) by 743 days.

(21) Appl. No.: 17/347,209

(22) Filed: Jun. 14, 2021

(65) Prior Publication Data

US 2022/0008581 A1 Jan. 13, 2022

Related U.S. Application Data

(60) Provisional application No. 63/038,820, filed on Jun. 14, 2020, provisional application No. 63/038,819, filed on Jun. 13, 2020.

(51) Int. Cl.
| | |
|---|---|
| *A61L 2/10* | (2006.01) |
| *A61L 2/24* | (2006.01) |
| *A61L 9/20* | (2006.01) |
| *A63B 71/00* | (2006.01) |

(52) U.S. Cl.
CPC ............... *A61L 2/10* (2013.01); *A61L 2/24* (2013.01); *A61L 9/20* (2013.01); *A63B 71/0036* (2013.01); *A61L 2202/11* (2013.01); *A61L 2202/14* (2013.01); *A61L 2202/25* (2013.01); *A61L 2209/11* (2013.01); *A61L 2209/12* (2013.01)

(58) Field of Classification Search
CPC ............................ A61L 2/10; A63B 71/0036
See application file for complete search history.

(56) References Cited

U.S. PATENT DOCUMENTS

| | | | |
|---|---|---|---|
| 2,249,473 A | 7/1941 | Jackson et al. | |
| 5,160,699 A | 11/1992 | Siegal | |
| 5,546,678 A | 8/1996 | Dhaemers | |
| 7,424,755 B1 * | 9/2008 | Montgomery | E03C 1/00 4/664 |
| 8,092,751 B2 | 1/2012 | Salvador Barea | |
| 8,779,385 B2 | 7/2014 | Noori | |

(Continued)

FOREIGN PATENT DOCUMENTS

| | | | |
|---|---|---|---|
| CN | 204709456 U | * | 10/2015 |
| CN | 204764334 U | | 11/2015 |

(Continued)

OTHER PUBLICATIONS

English Translation of CN 204709456 U provided by the European Patent Office Website espacenet.com: Xiaolong Liu; Remove Clean Passageway; Oct. 21, 2015 (Year: 2015).*

*Primary Examiner* — Kevin Joyner
(74) *Attorney, Agent, or Firm* — Plumsea Law Group, LLC (57) ABSTRACT

A static building structure may include an athletic facility. The facility may include a locker room area having disposed therein one or more lockers including ultraviolet lamps. In addition, the facility may include one or more high flow ultra high efficiency particulate air (HEPA) UV-C purifiers. Further, the athletic facility may have a shower area disposed adjacent the locker room area and including one or more far-UV-C lamps.

15 Claims, 8 Drawing Sheets

(56) References Cited

U.S. PATENT DOCUMENTS

| | | | |
|---|---|---|---|
| 9,289,527 | B1 | 3/2016 | Lichtblau |
| 9,339,570 | B2 | 5/2016 | Whitney |
| 11,690,924 | B1 * | 7/2023 | Gokcebay ................. A61L 2/26 250/455.11 |
| 2003/0034459 | A1 | 2/2003 | Bonin |
| 2010/0102253 | A1 | 4/2010 | Chang et al. |
| 2015/0158750 | A1 * | 6/2015 | Schiffmann ........... E03C 1/0404 422/107 |
| 2016/0158395 | A1 | 6/2016 | Hughes et al. |
| 2018/0371733 | A1 * | 12/2018 | Childress .................. A61L 2/10 |
| 2019/0070325 | A1 | 3/2019 | Preminger et al. |
| 2019/0209806 | A1 * | 7/2019 | Allen .................. H04L 12/2829 |
| 2019/0345711 | A1 * | 11/2019 | Hawkins .................. E04B 1/35 |

FOREIGN PATENT DOCUMENTS

| | | |
|---|---|---|
| CN | 205360037 U | 7/2016 |
| CN | 205360038 U | 7/2016 |
| CN | 106806915 | 6/2017 |
| CN | 107149308 | 9/2017 |
| CN | 208114353 U | 11/2018 |
| CN | 208480828 U | 2/2019 |
| CN | 110840093 | 2/2020 |
| KR | 20040033078 | 4/2004 |
| KR | 20060062660 | 6/2006 |
| KR | 20200028775 | 3/2020 |

\* cited by examiner

FACILITY DESIGN TO MINIMIZE VIRAL LOAD

CROSS-REFERENCE TO RELATED APPLICATIONS

This application claims priority to U.S. Provisional Patent Application No. 63/038,820, filed Jun. 14, 2020, and entitled Disinfecting Enclosures Using UV Light, the entire disclosure of which is incorporated herein by reference. This application also claims priority to U.S. Provisional Patent Application No. 63/038,819, filed Jun. 13, 2020, and entitled Facility Design to Minimize Viral Load, the entire disclosure of which is incorporated herein by reference.

BACKGROUND

The present disclosure is directed to a facility design to minimize viral load and, more specifically, to a static building structure having various features to reduce the risk of viral infection, particularly in an athletic locker room area.

Although some recommendations are to maintain six feet of distance between people to reduce risk of disease transmission (i.e., "social distancing"), some experts say this may not necessarily be effective in stopping the spread of disease, particularly in indoor environments. Some recommendations during times of high viral risk are for six feet of distancing between athlete lockers, with athletes wearing mask protection. This is not generally practical, easily applicable, cost effective, or truly impactful in control of pathogen spread. Upon entry to a locker room, e.g., at halftime or in between periods of play, athletes are often breathing heavily and not in a state of quiet respiration (a state assumed in typical six-foot distancing recommendations). Sweat and other bodily fluids from athletes have frequent contact with surfaces in a locker room area, and restroom facilities present a high-risk situation for aerosolization of pathogens. Locker rooms typically present inherently tight, high-risk spaces that require more creative strategic plans beyond traditional social distancing and shielding measures.

In addition, many janitorial protocols call for equipment and cleaning materials that have fragrances or other additive ingredients. However, the presence of cleaning products in the air can be harmful to the lungs, which can be detrimental to the performance of elite athletes. For elite athletes, even a small impact on a player's physiology has the potential to negatively impact athletic performance.

Further, fabric face coverings (masks) are not optimal for player recovery following strenuous exercise as they limit the ability for efficient carbon dioxide exchange. In addition, mask materials are typically absorbent, which poses an issue when a player is perspiring and breathing heavily. Once the mask gets wet, its effectiveness at reducing risk of communicating pathogens is reduced, as well as the player's ability to breathe while wearing it. Also, fabric masks are generally prohibitive to athlete rehydration. Further, masks cannot be worn in shower areas, and do not adequately protect the players' eyes from sprayed droplets or finger to eye transmission.

In addition, clothing and personal belongings are a high touch, high risk for the spread of pathogens. Athletic clothing and gear is of particularly high risk because of the amount of bodily secretions associated with sports, as well as the amount of physical contact between athletes. Further, the handling of laundry in a locker room can be a source of pathogen spread, as locker room staff often provide laundry services, including washing all player uniforms as well as towels, etc. In addition, some personal items, such as sunglasses or hats are worn on the face/head and present a high risk of transmission of pathogens. It is difficult to cleanse clothing and personal belongings with as much frequency as needed to minimize the risk of pathogen transmission.

Also, in the bathrooms, the toilet flushing process results in an aerosolized plume that presents increased risk for pathogen spread. In addition, sinks and soap dispensers can have contact surfaces that promote the spread of pathogens, as well. Further, shower areas present an environment including a large amount of moist air with more rapid spread of droplets.

The present disclosure addresses one or more of the issues identified above.

SUMMARY

In one aspect, the present disclosure is directed to a static building structure including an athletic facility. The facility may include a locker room area having disposed therein one or more lockers including ultraviolet lamps. In addition, the facility may include one or more high flow ultra high efficiency particulate air (HEPA) UV-C purifiers. Further, the athletic facility may have a shower area disposed adjacent the locker room area and including one or more far-UV-C lamps.

In another aspect, the present disclosure is directed to a method of minimizing viral load in an athletic facility locker room. The method may include cleansing surfaces without spraying disinfectants onto a cloth or the surface to be cleansed; wearing face shields while residing within the athletic facility; and utilizing third party verification to confirm that anti-viral protocols are being followed.

In another aspect, the present disclosure is directed to a disinfecting locker. The locker may include an enclosure including therein at least one UV-C lamp configured to irradiate the contents of the enclosure. In addition, the locker may include one or more UV-C transparent structures. Further, the locker may include one or more UV-C reflective surfaces.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The present disclosure is directed to a static building structure including various features to reduce the risk of viral infection. In particular, the description below is directed to implementation of risk reduction features and measures associated with an athletic locker room area. According to the present disclosure, locker rooms can be provided with several features and occupants can adopt various protocols to minimize the risk of infection. However, it will be understood that these measures may be applicable to other types of facilities. Thus, these features and protocols may be applicable various types of indoor facilities. For example, the features and protocols discussed below may be applicable to locker rooms and other changing areas, restroom/bathroom areas, athletic training rooms, fitness centers, weight rooms, conference rooms, video review rooms, and various other indoor areas associated with sports and athletic facilities and/or other types of indoor facilities.

Disinfecting Locker Design

Exemplary disinfecting lockers according to disclosed embodiment may have multiple disinfecting features, such as UV-C lighting, UV transparent shelving, and an electromechanical system configured to initiate operation of the UV lights when the door is closed and prevent operation of the UV lights when the door is open.

Figure 1:
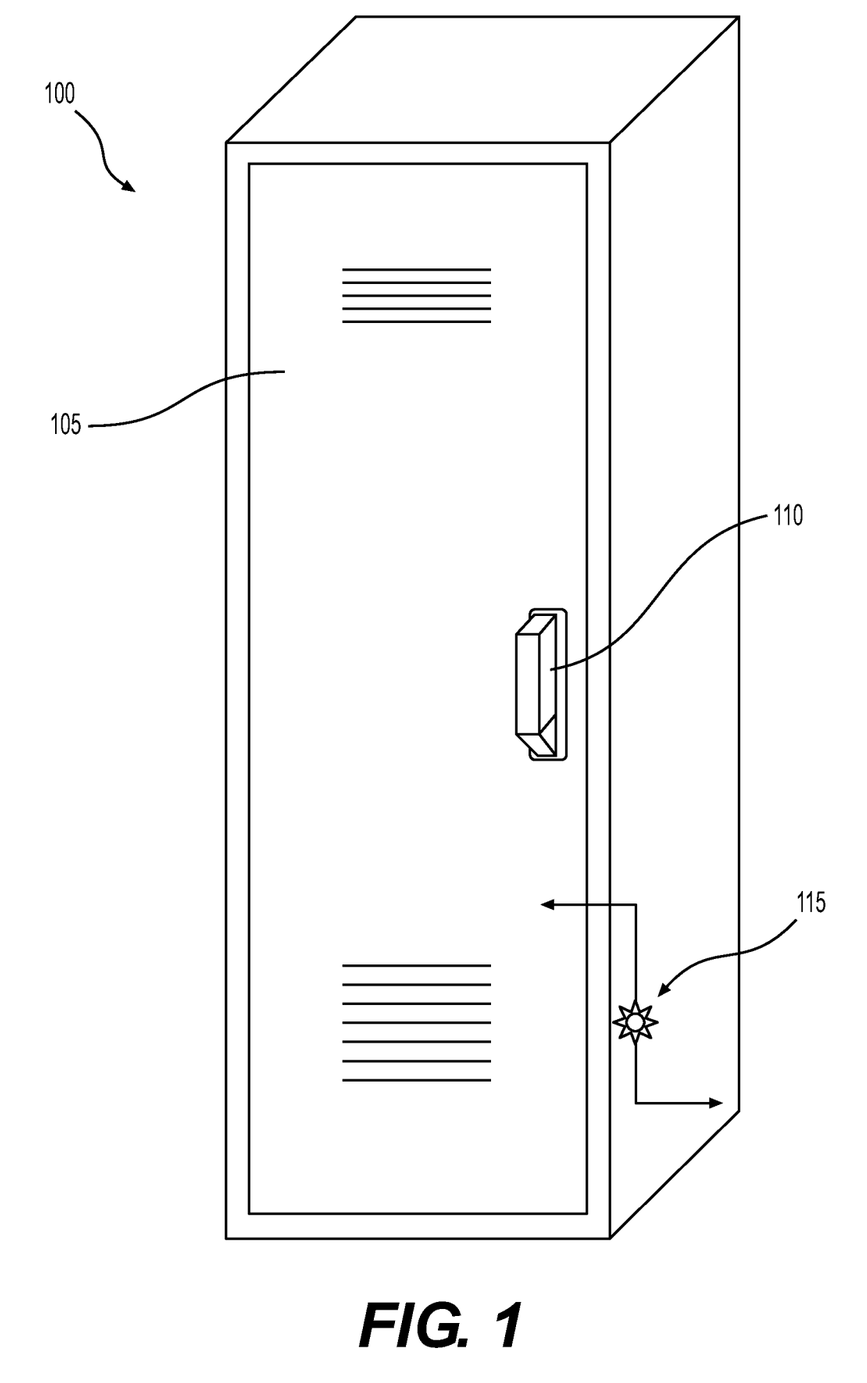
FIG. 1 is a schematic exterior perspective view of a locker according to a disclosed embodiment.

FIG. 1 is a schematic exterior perspective view of a locker according to a disclosed embodiment. FIG. 1 illustrates a locker 100. It will be understood that locker 100 may be any type of enclosure with any suitable size. In some embodiments, locker 100 may be sized for a person's belongings, such as clothing, sports equipment, shoes, and personal items, such as wallets, purses, glasses, jewelry, etc. In some embodiments, locker 100 may have an outer surface 100 that may be coated with a material having a low transmission rate for UV. In addition, high contact components of locker 100, such as a handle 110, may be formed of materials that have a short viral life, that is, materials upon which viruses do not live very long relative to other materials. An example of such materials usable for high contact components of locker 100 is copper. In some embodiments, such components may be formed of MRSA resistant plastic.

As also shown in FIG. 1, in some embodiments, locker 100 may include a UV-C light circuit 115. Circuit 115 may be configured to turn UV-C lamps inside locker 100 on when the door closes. In addition, Circuit 115 may be configured to turn the UV-C lamps off when the door of locker 100 opens. In order to effectuate such operation, locker 100 may include a device processor and a non-transitory computer readable medium including instructions executable by the processor. Such system may also be configured to keep the UV-C lamps on for a predetermined amount of time after the door closes.

Figure 2:
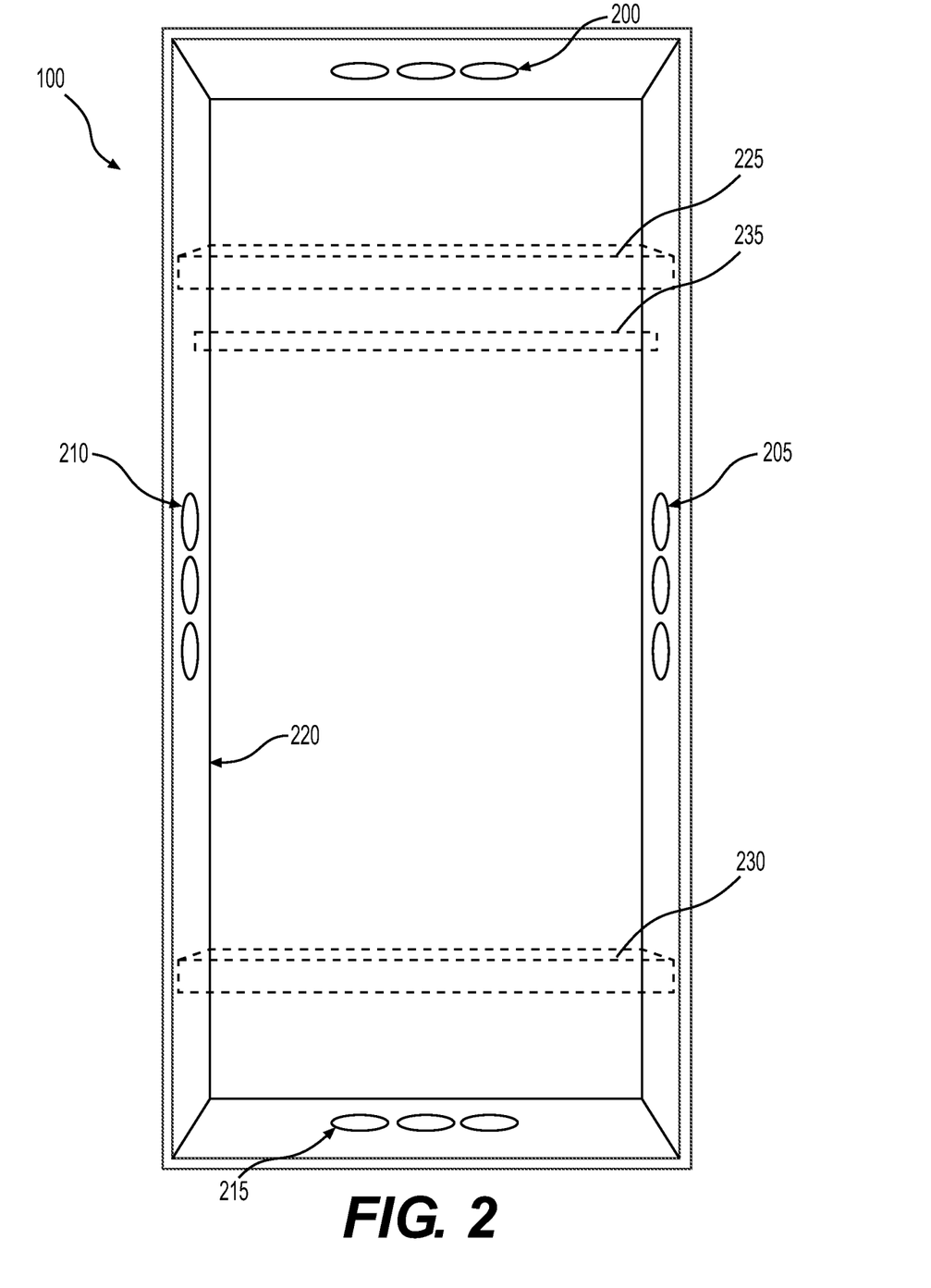
FIG. 2 is a schematic interior perspective view of a locker according to a disclosed embodiment.

FIG. 2 is a schematic interior perspective view of a locker according to a disclosed embodiment. The door of locker 100 has been omitted from FIG. 2 for clarity. As shown in FIG. 2, locker 100 may include UV-C lamps positioned strategically about the interior of the enclosure. For example, in some embodiments, locker 100 may include a first set of one or more UV-C lamps 200 positioned at the top of locker 100. In addition, locker 100 may include a second set of one or more UV-C lamps 205 located on one sidewall of the enclosure. Also, locker 100 may include a third set of one or more UV-C lamps 210 positioned on a second side wall of the enclosure. In some embodiments, locker 100 may also include a fourth set of one or more UV-C lamps 215 positioned on a bottom wall of the enclosure. It will be understood that fewer lamps or more lamps may be utilized within the enclosure. In some embodiments paneling may be utilized such that a common UV light source/panel may be used to illuminate multiple compartments.

The UV-C lamps used in the disclosed lockers may be configured to emit ultraviolet light with a wavelength in the range of 255 nm to 280 nm. In some embodiments, the lamps may be LED type lamps.

In order to facilitate the application of UV-C light to various areas of the enclosure, one or more walls of the enclosure may be reflective of UV-C light. For example, as shown in FIG. 2, locker 100 may include one or more mirrored walls 220. Alternatively, or additionally, one or more UV-C reflective panels may be positioned within the enclosure.

Also, in some embodiments, interior supports, such as shelves and/or clothes hanger rods may be formed of UV-C transparent material so as to avoid blocking the UV light from being delivered about the enclosure. An exemplary UV-C transparent material from which such supports may be formed is quartz. For example, as shown in FIG. 2, locker 100 may include an upper shelf 225 formed of UV-C transparent material. Alternatively, or additionally, locker 100 may include a lower shelf 230 formed of UV-C transparent material. Further, in some embodiments, locker 100 may include a dowel rod 235 formed of UV-C transparent material.

In some embodiments, UV-C transparent shelving may be utilized in order to sanitize the underside of the user's belongings. For example, in some embodiments, a UV-C lamp may be positioned directly under a UV-C transparent shelf in order to disinfect the underside of the user's glasses or the soles of their shoes.

Figure 3:
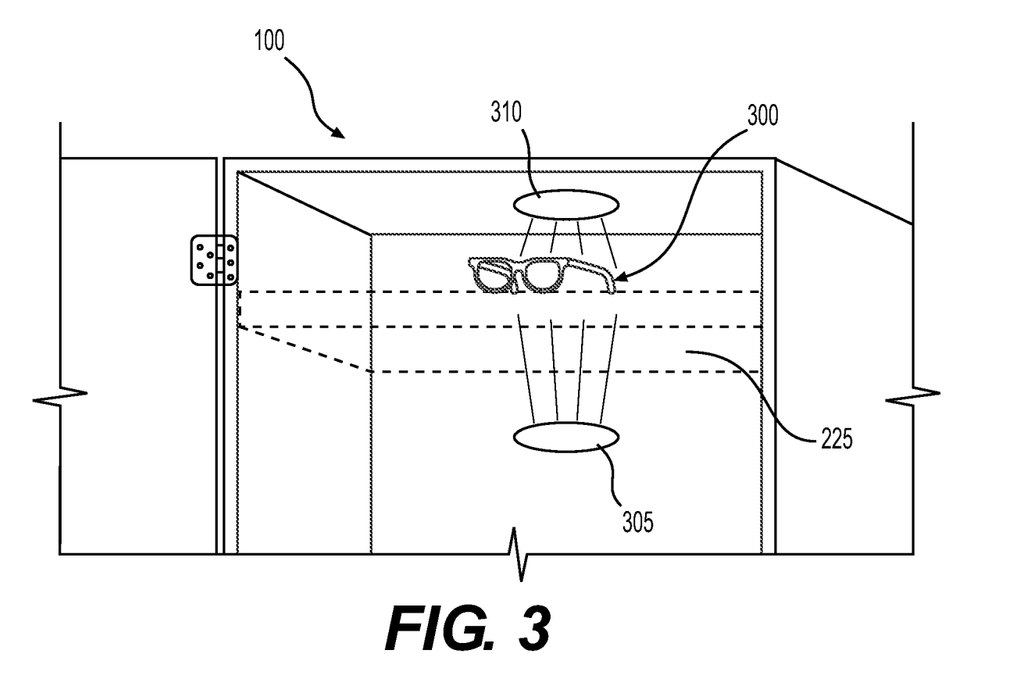
FIG. 3 is a schematic perspective view of an upper interior portion of a locker according to a disclosed embodiment.

FIG. 3 is a schematic perspective view of an upper interior portion of a locker according to a disclosed embodiment. As shown in FIG. 3, locker 100 may include UV-C transparent upper shelf 225. In addition, in order to disinfect the underside of personal belongings, such as a pair of glasses 300, a UV-C lamp 305 may be positioned directly under UV-C transparent upper shelf 225. UV-C light from lamp 305 may be shone directly through shelf 225 onto the belongings stored thereon. As also shown in FIG. 3, in some embodiments, a UV-C lamp 310 may be mounted above shelf 225 to irradiate the belongings from above. UV-C lamp 310 may be provided in addition to, or in lieu of, lamp 305.

Figure 4:
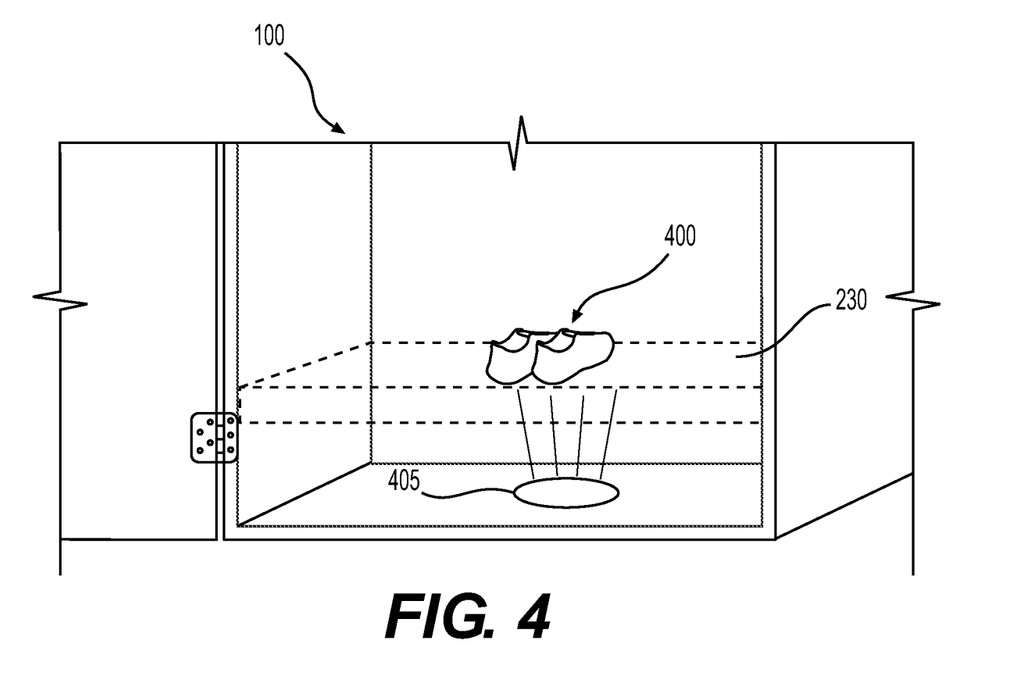
FIG. 4 is a schematic perspective view of a lower interior portion of a locker according to a disclosed embodiment.

FIG. 4 is a schematic perspective view of a lower interior portion of a locker according to a disclosed embodiment. As shown in FIG. 4, locker 100 may include UV-C transparent lower shelf 230 upon which the user may store their shoes 400 (which may include casual shoes, cleats, or other footwear). In order to disinfect the soles of these shoes 400, a UV-C lamp 405 may be positioned directly under UV-C transparent lower shelf 230.

The locker may also include a locking system with automatic locking and unlocking. For example, the system may include a detection device, such as a proximity sensor, that detects the presence of a fob carryable by a user. When the fob comes within a few feet of the locker, the locker may unlock automatically. When the fob is taken more than a few feet away from the locker, the locker may lock automatically. In some embodiments, the system may be configured to detect the proximity of a smartphone of a user. In some embodiments, there may be a feature where one can wave a foot or hand near a portion of the locker and it will unlock and possibly open.

Figure 5:
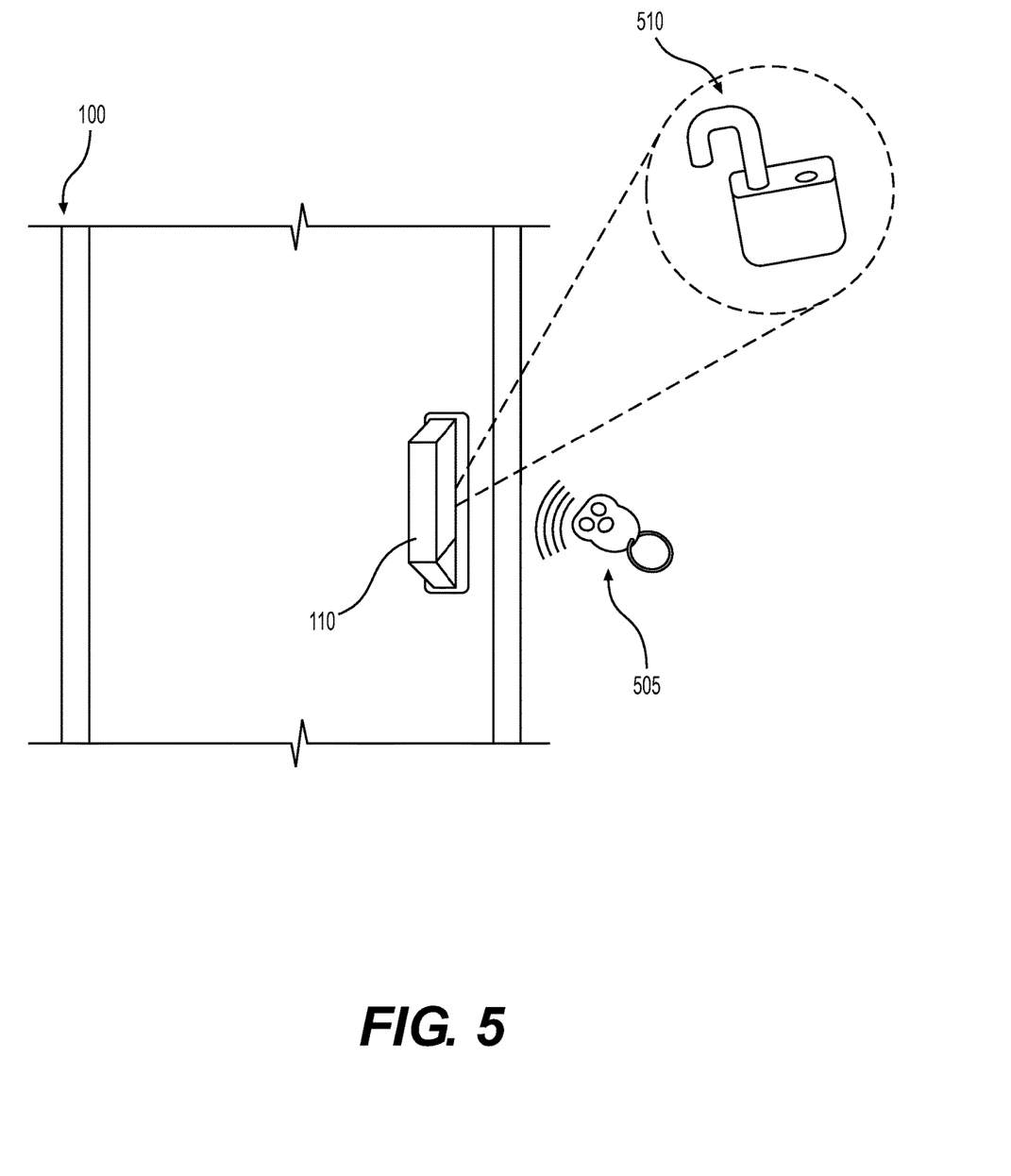
FIG. 5 is a schematic illustration of an automatic unlocking system of a locker according to a disclosed embodiment.

In some embodiments, FIG. 5 is a schematic illustration of an automatic unlocking system of a locker according to a disclosed embodiment. As shown in FIG. 5, locker 100 may include a locking system associated with handle 110. The user of locker 100 may have a fob 505 which, when brought within a predetermined proximity of the locker will automatically unlock the locker, as illustrated by an unlocked symbol 510. This system may not only unlock the locker, but may turn off the UV-C lamps inside and open the locker. This minimizes the amount the user must touch the surfaces of the locker. In some embodiments, the fob may include controls, such as buttons, with which the user may lock, unlock, open, and close the locker. Alternatively, or additionally, the fob may include user controls for turning the UV-C lamps on and/or off.

Gear Sanitization

In some embodiments, sports-specific equipment that is difficult to cleanse may be storable in a dedicated UV-C enclosure. For example, football helmets and padding cannot be laundered with uniforms and other clothing. A locker may be configured with one or more compartments dedicated for irradiating such equipment with UV-C light.

Figure 6:
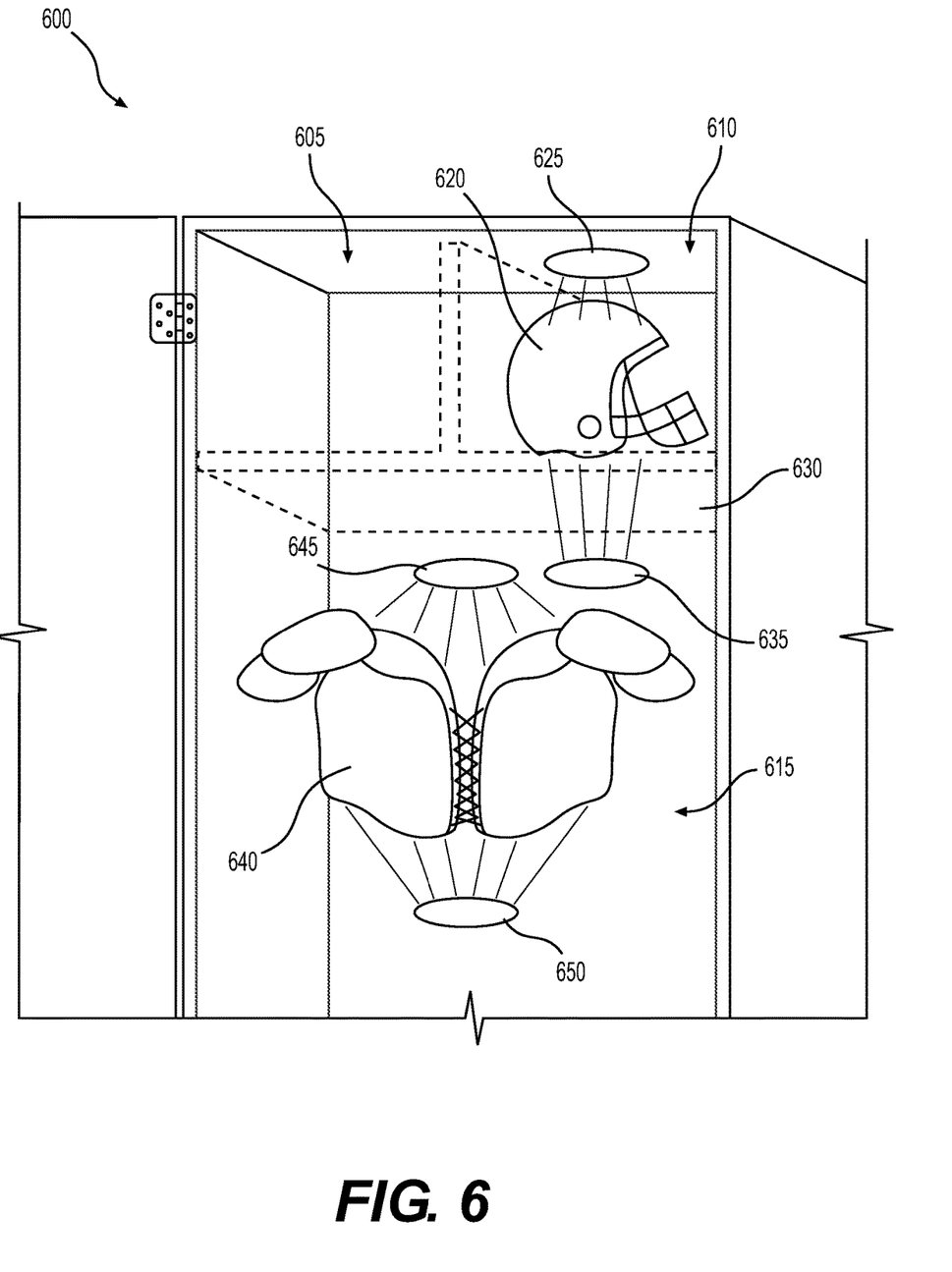
FIG. 6 is a schematic perspective interior view of a locker with sport-specific equipment compartments according to a disclosed embodiment.

FIG. 6 is a schematic perspective interior view of a locker with sport-specific equipment compartments according to a disclosed embodiment. As shown in FIG. 6, a locker 600 may include several compartments, such as a first compartment 605, a second compartment 610, and a third compartment 615. As further shown in FIG. 6, one or more of these compartments may be sized and configured to house and disinfect particular sports equipment. For example, in some embodiments, second compartment 610 may be configured to house and disinfect a football helmet 620.

As shown in FIG. 6, helmet 620 may be irradiated by one or more UV-C lamps strategically placed about second compartment 610. For example, second compartment 610 may include a first UV-C lamp 625 above helmet 620. In addition, a second UV-C lamp 635 may be positioned directly under a UV-C transparent shelf 630 and thereby configured to irradiate the underside and interior of helmet 620. In some embodiments, second compartment 610 may include a UV-C lamp on shelf 630 that protrudes up into the interior of helmet 620 (see FIG. 7). In some embodiments, second compartment 610 may include other locker features disclosed herein, such as UV-C reflective surfaces, UV-C transparent structures, etc.

Similarly, third compartment 615 may be configured to house and disinfect football shoulder pads 640, and possibly other padding. As shown in FIG. 6, third compartment 615 may include an upper UV-C lamp 645 configured to irradiate from above, and a lower UV-C lamp 650 configured to irradiate from below and into the interior of shoulder pads 640. Third compartment 615 may also include other locker features disclosed herein, such as UV-C reflective surfaces, UV-C transparent structures, etc.

Figure 7:
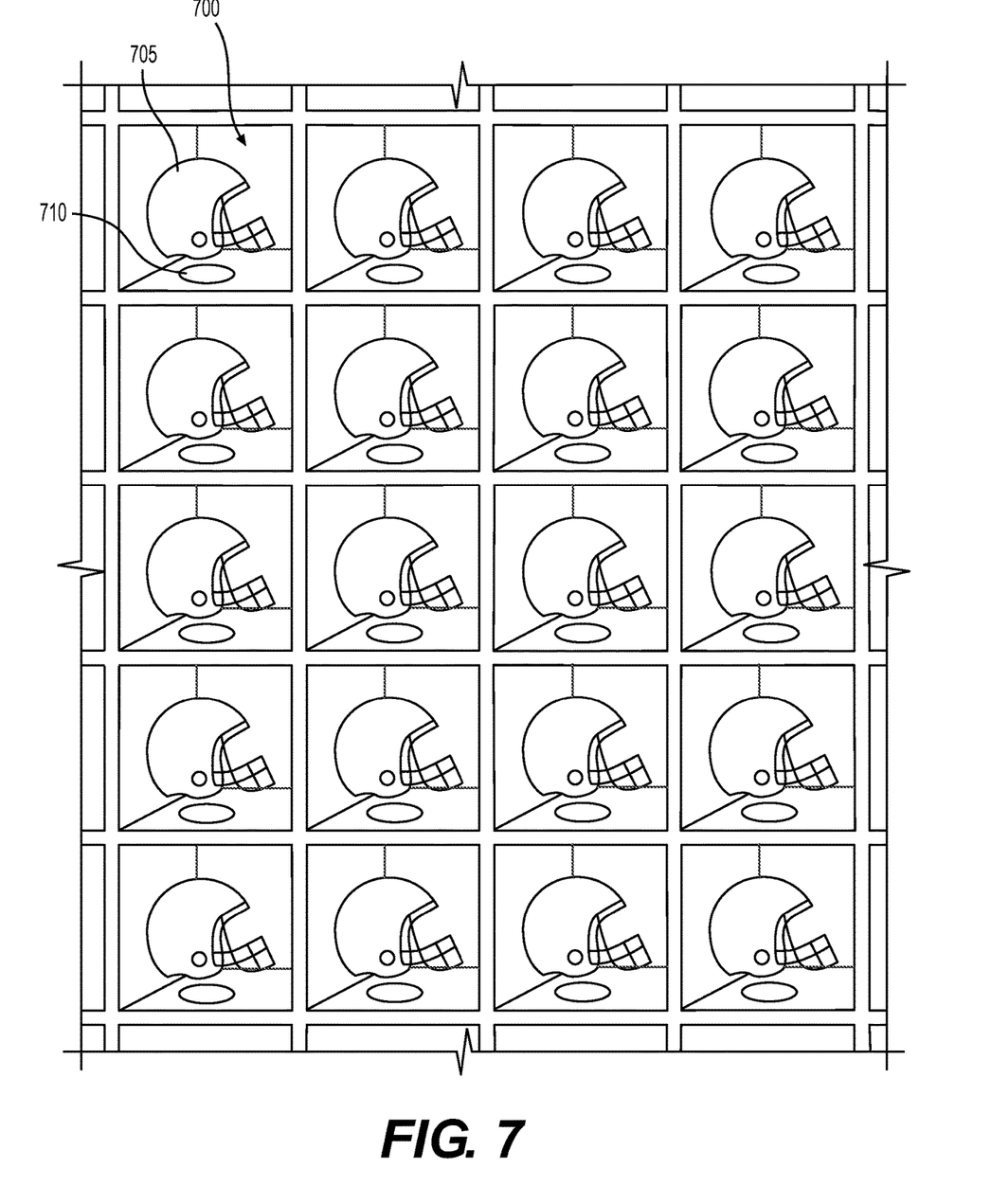
FIG. 7 is a schematic illustration of a wall of compartments configured to house and disinfect football helmets.

In some cases, certain equipment may be located in its own dedicated area. For example, FIG. 7 is a schematic illustration of a wall of compartments configured to house and disinfect football helmets. It will be understood that each of these compartments has its own door to enclose the compartment. In some embodiments, a single door may enclose multiple compartments. The compartment door(s) are omitted from FIG. 7 for clarity.

As shown in FIG. 7, a first enclosure 700 has housed therein a football helmet 705. A UV-C lamp 710 is provided at the bottom of the compartment and shines upward into the interior of the helmet. For example, the helmet may sit on a surface right over top of the lamp. In some embodiments, the helmet may sit on a UV transparent shelf and the UV-C lamp may shine upwards through the shelf into the helmet, similar to that shown in FIG. 6. It will be understood that compartments like this may be provided for other types of equipment, such as knee pads, elbow pads, etc.

Facility Configuration

Figure 8:
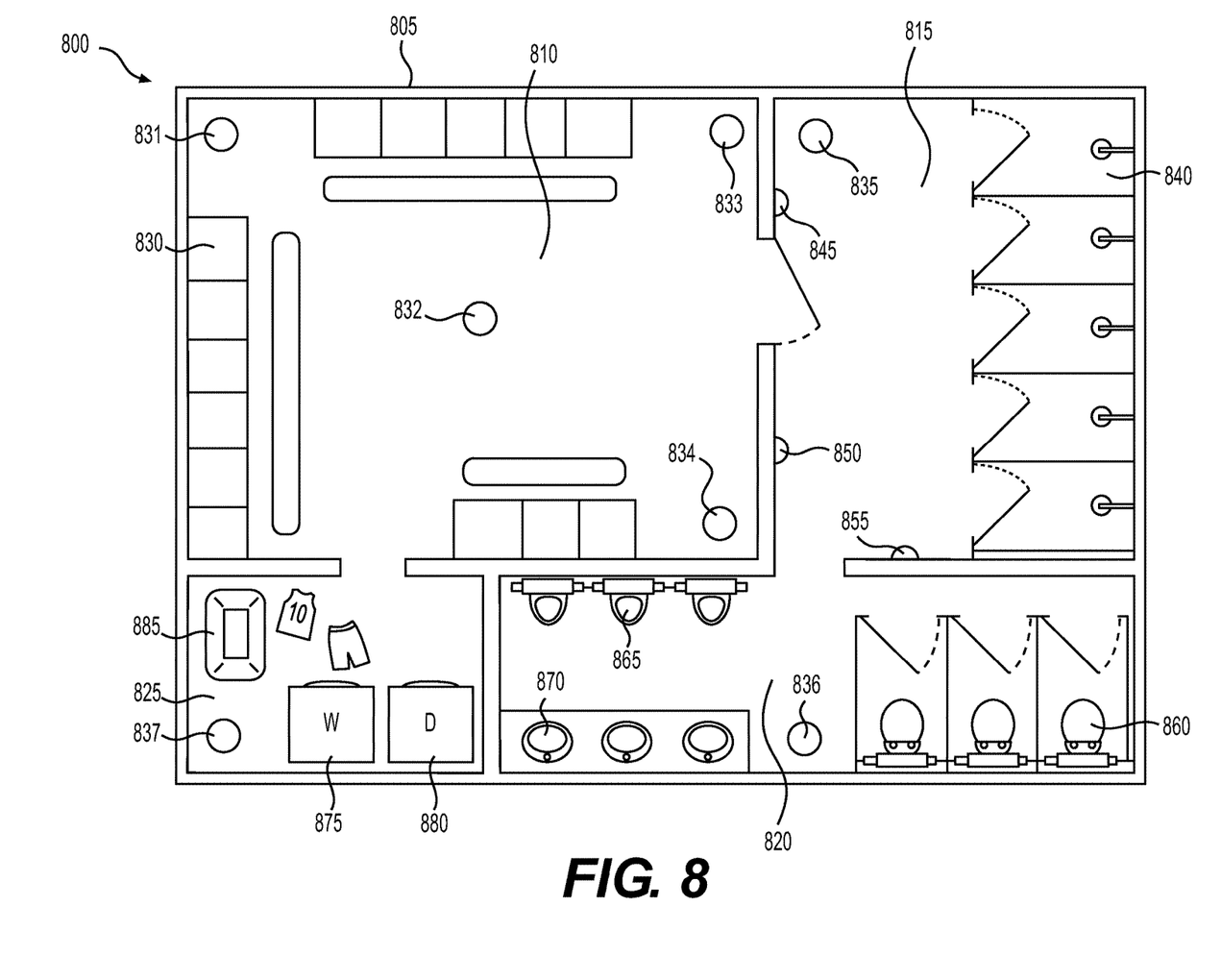
FIG. 8 is a schematic illustration of a floor plan for a static building structure including at least an athletic locker room and associated areas.

Anti-viral lockers, such as those discussed above, may be incorporated into an athletic facility, e.g., a locker room. FIG. 8 is a schematic illustration of a floor plan for a static building structure including at least an athletic locker room and associated areas. As shown in FIG. 8, a static building structure 800 may include a plurality of areas/rooms partitioned off by a plurality of walls 805. For example, walls 805 may define a locker room area 810 having disposed therein one or more lockers 830 including ultraviolet lamps, as discussed above. The configuration and layout of the locker room may vary. That shown in FIG. 8 is intended to be schematic and exemplary only. As shown in FIG. 8, adjacent locker room area 810 may be several areas associated with a locker room such as, for example, a shower area 815, a toilet area 820, and a laundry area 825. In some embodiments, static building structure 800 may include other areas/rooms, whereas, in other embodiments, static building structure 800 may consist essentially of a locker room area, a shower area, a toilet area, and a laundry area.

Airflow

Rather than utilizing harsh cleaning products that could be damaging to athletes' lungs, efforts should be made to keep cleaning products as nontoxic as possible and avoid unnecessary inhalation of substances. One way to provide disinfection without harsh cleaning products is to improve air quality using high flow ultra high efficiency particulate air (HEPA) UV-C (ultraviolet lamp) purifier units. This equipment can be easily retrofitted in existing locker rooms as these units can be brought in and simply plugged into a preexisting electrical outlet. These units have the ability to turn over room air within the locker room at a rapid pace (within minutes), and are viricidal to pathogens in the air. This not only minimizes contact of droplets with players' faces, but also minimizes the volume of droplets potentially settling on the ground and other surfaces.

Moreover, along with the use of these units, airflow analysis is conducted for site-specific flow patterns, ensuring that air flow is directed away from individuals. In general, the pattern of flow of air down the row of lockers across multiple players is to be avoided. Units are strategically placed such that air is drawn away from people rather than crossing through a group. Specific room volume is matched with an appropriate unit or units to ensure strategic laminar flow of air away from personnel. Further, units are strategically placed specific to the room to control airflow.

As shown in FIG. 8, locker room area 810 may include several, strategically placed HEPA UV-C purifiers. For example, locker room area 810 may include a first HEPA UV-C unit 831, a second HEPA UV-C unit 832, a third HEPA UV-C unit 833, and a fourth HEPA UV-C unit 834. The locations of these units are intended to be both schematic and exemplary only. The placement of these purifiers may vary according to the factors discussed above. In addition, these units are merely shown schematically as circles. It will be under stood that the shape, size, and general configuration of the HEPA UV-C units may vary.

In addition, the other adjacent areas may include additional HEPA UV-C units. For example, in some embodiments, shower area 815 may include a fifth HEPA UV-C unit 835. In some embodiments, toilet area 820 may include a sixth HEPA UV-C unit 836. Further, in some embodiments, laundry area 825 may include a seventh HEPA UV-C unit 837.

Shower Area

In order to keep up with the high moisture environment in the shower area, the shower area may include one or more far-UV-C lamps in the ceiling or walls. Far-UV-C has the ability to maintain germicidal properties, while remaining safe for human exposure. As shown in FIG. 8, shower area 815 may include a plurality of far-UV-C lamps. For example, as shown in FIG. 8, shower area 815 may include a first far-UV-C lamp 845, a second far-UV-C lamp 850, and a third far-UV-C lamp 855. It will be understood that the shape, size, and locations of these far-UV-C lamps is schematic and exemplary only. In some embodiments, it may be desirable to locate such lamps in the ceiling above each shower stall.

Laundry

A designated separate area for dirty linen placement is provided. In addition, separate staff wearing higher level PPE are to be responsible for properly removing and washing soiled linen. As shown in FIG. 8, laundry area 825 may be located adjacent to, but separate from, locker room area 810. Laundry area 825 may be configured to handle laundry. For example, as shown in FIG. 8, laundry area 825 may include a clothes washer 875 and a clothes dryer 880. In addition, a laundry cart 885 may be provided for the athletes to place their dirty laundry items. As shown, an open doorway enables passage between the two areas. A door is not necessarily required. However, in some embodiments, a door may be included in order to provide additional separation of the laundry from the athletes and others in locker room area 810. The players may place their dirty laundry on the floor of laundry area 825 or in laundry cart 885. This practice takes the collection/pile of dirty laundry out of locker room area 810 where the athletes are and moves it to a separate area.

Bathroom Protocols

In order to prevent the plume of droplets created by flushing toilets, the disclosed toilets may include a feature that prevents flushing unless the lid is down. As shown in FIG. 8, toilet area 820 may include a plurality of toilets 860. Each of toilets 860 may be equipped with a flush mechanism that requires a toilet lid to be covering the toilet bowl in order for the flush mechanism to operate.

In addition, toilet area 820 may include one or more urinals 865 that are continuous flow or no flow in order to avoid the flush mechanism altogether. Further, all sinks (870) and soap dispensers may have no-touch operation. For example, sinks 870 may be motion activated for touchless use.

Surface Control

In conjunction with airflow and air treatment, the cleaning of locker room surfaces is to be done often. Surfaces will be regularly wiped specifically with products that do not have fragrances, additives, or unnecessary ingredients. For example, simple solutions of water and 70% alcohol may be used as an option that is both economical and non-toxic. Any possible skin irritant or substance that may cause a skin hypersensitivity reaction over time is to be avoided. Further, whenever possible, cleaning solution is to be put on a cloth and the cloth will be used to wipe surfaces. This minimizes fumes in the locker room environment.

In addition, any new proposed floor cleaning products are to be pre-tested in order to ensure that the product does not build up on cleats in a manner that makes their use less effective. For example, products may be tested to ensure that cleaning products on the soles of cleated shoes do not cause the cleats to become clogged with dirt and mud more easily.

Also, aerosolized products, sprayers, and ozone products are not to be used during times when athletes access the locker rooms, and can only be used when there is an abundance of time far beyond the minimum requirements prior to the athletes accessing the locker rooms, in order to allow sufficient time for adequate air exchange in the space to occur prior to player reentry.

Personal Protection

In lieu of fabric or paper masks, face shields are to be used by the players. Face shields stop droplets from spreading from a person's mouth to the adjacent surroundings. In addition, they protect the wearer's eyes, nose, and mouth from droplets in the environment. Further, face shields can allow rapid exchange of carbon dioxide, as they do not inhibit the athletes' breathing as much as a fabric mask. It will also be noted that face shields can be waterproof, easily reused, and extremely cost effective. While using face shields, players can communicate clearly with one another, easily move to the showers or restrooms, and even sip a beverage to rehydrate using a straw.

Proper sizing of face shields is to be utilized. In particular, face shields should extend below the chin anteriorly, to the ears laterally, and there should be no exposed gap between the forehead and the shield's headpiece.

In some sports that require helmets, an athlete can place on a face shield immediately upon removing their helmet, and wear this shield throughout all locker room activities ensuring uncompromised and continuous protection.

Validation

In order to ensure successful adaptation of these protocols in the locker room environment, the techniques described above may be validated by a third party. For example, the third party may test air quality for safety and surfaces for traces of pathogen.

This strategic plan features elements that are widely applicable to a variety of locker room designs. A large remodel is not necessary for successful implementation. As described above, locker room design requires high attention to detail of air, surfaces and the athletes. While traditional six-foot distancing measures may not be effective or practical in a locker room setting, strategic use of germicidal technology, cleaning techniques, and personal protective equipment (PPE) allows for a safe and clean environment without compromising the athletic abilities of the player.

Figure 9:
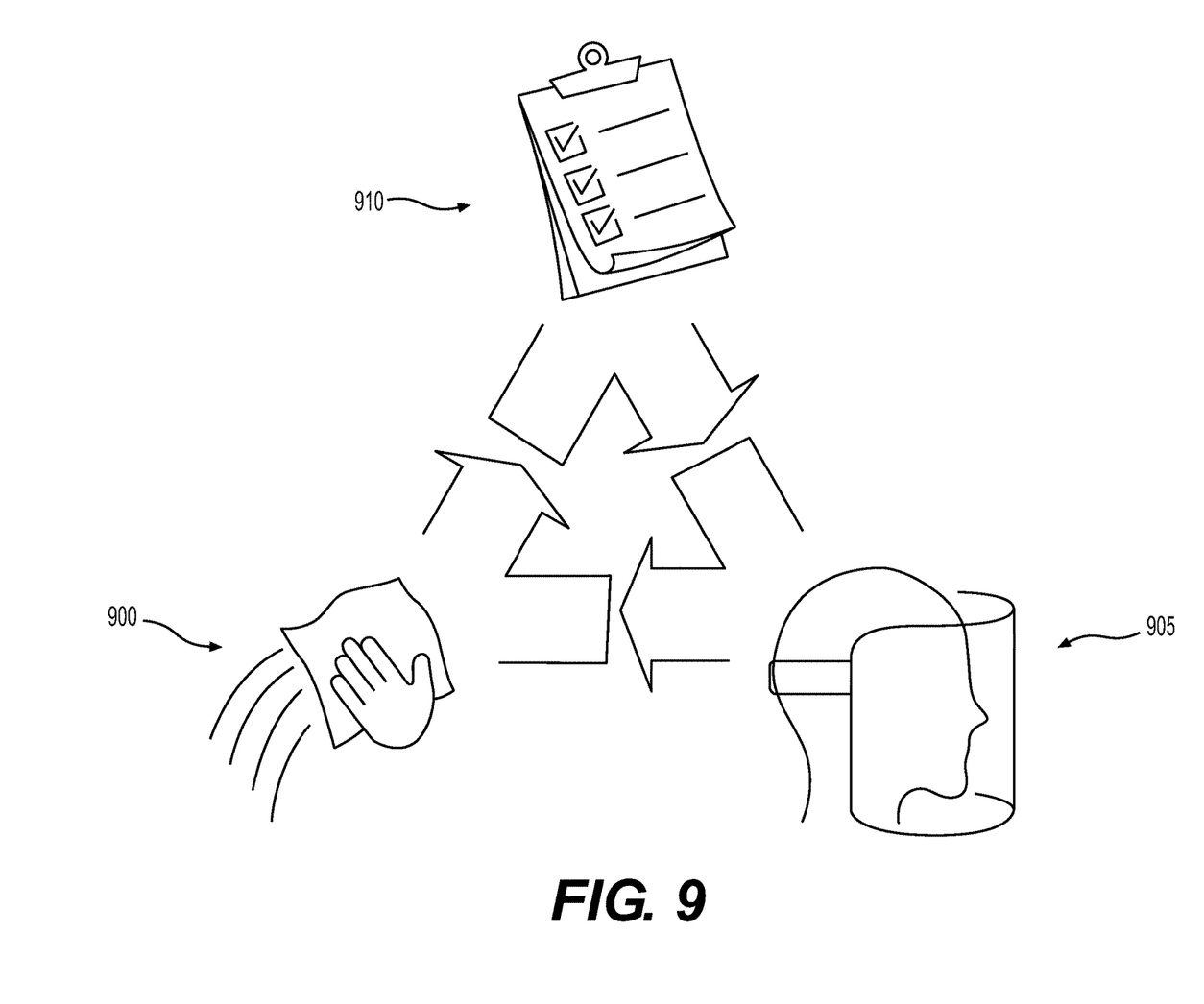
FIG. 9 is a schematic illustration of protocols recommended to be followed in order to minimize risk of disease transmission in an athletic locker room facility.

FIG. 9 is a schematic illustration of protocols recommended to be followed in order to minimize risk of disease transmission in an athletic locker room facility. As shown in FIG. 9, surface cleaning protocols 900 should be followed. For example, surfaces should be cleaned without spraying disinfectants onto a cloth or the surface to be cleansed. In addition, personal protective equipment (PPE) should be used by persons within the locker room, including the athletes. In particular, as discussed above, athletes should use face shields, as illustrated by icon 905 in FIG. 9.

As also shown in FIG. 9, disease prevention protocols may include utilizing third party verification, as indicated by icon 910 in FIG. 9, to confirm that anti-viral protocols are being followed. For example, in some embodiments, confirming that anti-viral protocols are being followed may include third party performance of air quality testing. In some embodiments, confirming that anti-viral protocols are being followed may include third party performance of surface testing for pathogens. Also, disease prevention protocols may include performing predetermined cleaning tasks when the locker room is empty except for cleaning staff.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A static building structure including an athletic facility, comprising:
    a locker room area having disposed therein one or more lockers including ultraviolet lamps;
    the athletic facility including one or more high flow ultra high efficiency particulate air (HEPA) UV-C purifiers;
    the athletic facility further having a shower area disposed adjacent the locker room area and including one or more far-UV-C lamps; and
    a disinfecting locker, comprising:
    an enclosure including therein at least one UV-C lamp configured to irradiate the contents of the enclosure;
    one or more UV-C transparent structures; and
    one or more UV-C reflective surfaces;
    wherein the UV-C lamp is independent of the UV-C transparent structures.

2. The static building structure of claim 1, further including one or more toilets having a flush mechanism that requires a toilet lid to be covering the toilet bowl in order for the flush mechanism to operate.

3. The static building structure of claim 1, further including one or more urinals having a continuous flow or no flow.

4. The static building structure of claim 1, further including one or more sinks having no-touch operation.

5. The static building structure of claim 1, including a laundry area adjacent to, but separate from, the locker room area, and configured for handling of laundry.

6. The static building structure of claim 1, wherein at least one of the shower area, a toilet area, and a laundry area includes one or more high flow ultra high efficiency particulate air (HEPA) UV-C purifiers.

7. The static building structure of claim 1, wherein the locker further includes a handle formed of short viral life material.

8. The static building structure of claim 7, wherein the short viral life material is copper.

9. The static building structure of claim 7, wherein the short viral life material is an MRSA resistant plastic.

10. The static building structure of claim 1, further including a UV-C light circuit configured to automatically turn UV-C lamps off when the door to the locker opens and automatically turn the UV-C lamps on when the door closes.

11. The static building structure of claim 1, wherein the one or more UV-C transparent structures include a UV-C transparent shelf; and
    wherein at least one UV-C lamp is positioned below the UV-C transparent shelf and is configured to irradiate any items stored on the shelf by directing UV-C light through the shelf.

12. The static building structure of claim 1, wherein the locker further includes a mechanism by which the locker unlocks upon the user coming within a predetermined distance of the locker.

13. The static building structure of claim 12, wherein the mechanism by which the locker unlocks includes a detection device affixed to a structure of the locker, and a fob carryable by a user and detectable by the detection device.

14. The static building structure of claim 12, wherein the mechanism by which the locker unlocks includes a detection device affixed to a structure of the locker, wherein a smartphone of a user is configurable to be detectable by the detection device.

15. The static building structure of claim 1, wherein the locker includes one or more compartments configured to house and disinfect sport-specific equipment.

* * * * *